(12) United States Patent
Chen et al.

(10) Patent No.: US 6,982,281 B1
(45) Date of Patent: Jan. 3, 2006

(54) PHARMACEUTICAL COMPOSITIONS AND DOSAGE FORMS FOR ADMINISTRATION OF HYDROPHOBIC DRUGS

(75) Inventors: Feng-Jing Chen, Salt Lake City, UT (US); Mahesh V. Patel, Salt Lake City, UT (US)

(73) Assignee: Lipocine Inc, Salt Lake City, UT (US)

( * ) Notice: Subject to any disclaimer, the term of this patent is extended or adjusted under 35 U.S.C. 154(b) by 849 days.

(21) Appl. No.: 09/716,029

(22) Filed: Nov. 17, 2000

(51) Int. Cl.
*A61K 31/355* (2006.01)
*A61K 31/35* (2006.01)
*A61K 31/235* (2006.01)
*A61K 9/48* (2006.01)
*A61K 9/66* (2006.01)

(52) U.S. Cl. .................. 514/458; 514/456; 514/543; 424/451; 424/452; 424/455

(58) Field of Classification Search ............... 514/543, 514/458, 456; 424/455, 451, 452
See application file for complete search history.

(56) References Cited

U.S. PATENT DOCUMENTS

| | | | |
|---|---|---|---|
| 4,895,726 A | 1/1990 | Curtet et al. | |
| 4,925,672 A | 5/1990 | Gremm et al. | |
| 4,961,890 A | 10/1990 | Boyer | |
| 5,545,628 A | 8/1996 | Deboeck et al. | |
| 5,593,971 A | 1/1997 | Tschollar et al. | |
| 5,827,536 A | 10/1998 | Laruelle | |
| 5,880,148 A | 3/1999 | Edgar et al. | |
| 5,883,109 A | 3/1999 | Gregg et al. | |
| 5,981,586 A | 11/1999 | Pershadsingh | |
| 6,027,747 A | 2/2000 | Terracol et al. | |
| 6,042,847 A | 3/2000 | Kerĉ et al. | |
| 6,057,339 A | 5/2000 | Gregg | |
| 6,066,653 A | 5/2000 | Gregg et al. | |
| 6,074,670 A | 6/2000 | Stamm et al. | |
| 6,096,338 A | 8/2000 | Lacy et al. | |
| 6,180,138 B1 | 1/2001 | Engh et al. | |
| 6,248,363 B1 * | 6/2001 | Patel et al. | 424/97 |

FOREIGN PATENT DOCUMENTS

| | | |
|---|---|---|
| EP | 0724877 A1 | 8/1996 |
| JP | 5194209 | 8/1993 |
| JP | 11152227 | 6/1999 |
| WO | WO 82/01649 | 5/1982 |
| WO | WO97/04749 A1 * | 2/1997 |
| WO | WO 98/30205 | 7/1998 |
| WO | WO 99/29300 | 6/1999 |
| WO | WO 99/40904 | 8/1999 |
| WO | WO 00/16749 | 3/2000 |
| WO | WO 00/37057 | 6/2000 |
| WO | WO 00/50007 | 8/2000 |
| WO | WO 00/57859 | 10/2000 |
| WO | WO 00/57918 | 10/2000 |
| WO | WO 00/7289 | 12/2000 |
| WO | WO 00/72825 | 12/2000 |
| WO | WO 00/76482 | 12/2000 |
| WO | WO 01/49262 | 7/2001 |

\* cited by examiner

*Primary Examiner*—Zohreh Fay
*Assistant Examiner*—Brian-Yong Kwon
(74) *Attorney, Agent, or Firm*—Dianne E. Reed; Reed & Associates

(57) ABSTRACT

Pharmaceutical compositions and dosage forms for administration of hydrophobic drugs, particularly fenofibrate, are provided. The compositions comprise a therapeutically effective amount of an active agent and a solubilizer. The solubilizer is selected to effectively solubilize active agent in the composition. The solubilizers employed as part of the invention include: a vitamin E substance; monohydric alcohol esters such as trialkyl citrates, lactones and lower alcohol fatty acid esters; nitrogen-containing solvents; phospholipids; glycerol acetates such as acetin, diacetin and triacetin; glycerol fatty acid esters such as mono-, di- and triglycerides and acetylated mono- and diglycerides; propylene glycol esters; ethylene glycol esters; and combinations thereof. The pharmaceutical dosage forms contain the compositions in a suitable dosage form unit such as a capsule. Methods of treating patients comprising administering the compositions are also provided.

33 Claims, No Drawings

PHARMACEUTICAL COMPOSITIONS AND DOSAGE FORMS FOR ADMINISTRATION OF HYDROPHOBIC DRUGS

TECHNICAL FIELD

The present invention relates generally to the delivery of hydrophobic drugs, and more specifically relates to novel pharmaceutical compositions in which a hydrophobic drug, particularly fenofibrate, is formulated to improve patient compliance and/or bioavailability following oral administration. The invention has utility in the fields of pharmaceutical formulation, pharmacology and medicine.

BACKGROUND

Numerous therapeutic agents are poorly soluble in an aqueous medium. Conventional formulations that incorporate unmilled or non-micronized forms of these therapeutic agents suffer from several disadvantages such as incomplete dissolution, slow dissolution and/or highly variable dissolution profiles. Furthermore, following oral administration, these conventional formulations exhibit low and/or variable bioavailability. To compensate for low bioavailability, the dose is often increased in these formulations. Dosage increases, however, still do not address the problems associated with highly variable inter- and/or intra-subject bioavailability. Thus, conventional formulations of hydrophobic drugs are frequently required to be taken with meals in order to address poor bioavailability, in addition to the variability associated with the bioavailability encountered with these drugs. As a result, however, patient compliance is often low as patients may forget to administer these formulations with meals or decide to skip a dose when the patient is not willing to consume an entire meal.

Poor patient compliance, in turn, requires frequent monitoring and dosage adjustments by the treating clinician. In particular, these disadvantages are evidenced with several families of lipid-regulating agents, such as fibrates and statins.

Fenofibrate (2-[4-(4-chlorobenzoyl)phenoxy]-2-methylpropanoic acid, 1-methylethylester) is a well known lipid-regulating agent from the fibrate family. The active metabolite of fenofibrate, fenofibric acid, produces reductions in total cholesterol, low density lipoprotein (LDL), apolipoprotein B, total triglycerides and very low density lipoprotein (VLDL). In addition, treatment with fenofibrate results in increases in high density lipoprotein (HDL).

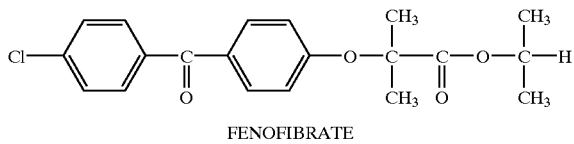

FENOFIBRATE

Fenofibrate is hydrophobic in nature (see structure shown above) and is practically insoluble in water. Fenofibrate has been commercially available under the names Lipanthyl, Lipidil® and Lipantil. Although the usual daily dose is as high as 300–400 mg, the product is nonetheless poorly absorbed in the gastrointestinal tract of patients. As a result, it is poorly and variably bioavailable and must be taken with food.

One approach in producing pharmaceutically acceptable fenofibrate hydrophobic formulations involves the use of micronization. U.S. Pat. No. 4,895,726 to Curtet et al. discloses a composition and method of improving the dissolution, and consequently, the bioavailability, of fenofibrate by using a solid surfactant that is co-micronized with fenofibrate. U.S. Pat. No. 5,880,148 to Edgar et al. also discloses a combination of a micronized mixture of fenofibrate with a solid surfactant and a vitamin E substances. This combination is stated to be useful as an antiatheromatous drug and to exhibit a synergistic effect by protecting plasma LDL from oxidation. U.S. Pat. No. 4,800,079 to Boyer et al. discloses a controlled-release formulation of fenofibrate based on specially designed granules. Each granule contains an inert core, a fenofibrate layer and a protective layer. The formulation is characterized in that fenofibrate is present in the form of crystalline microparticles of dimensions not greater than 30 microns. The microparticles are included within the pores of an inert matrix. U.S. Pat. No. 6,074,670 to Stamm et al. discloses an immediate-release fenofibrate composition comprising an inert hydrosoluble carrier covered with at least one layer containing fenofibrate in a micronized form having a size less than 20 microns.

In the United States, fenofibrate is currently available under the name Tricor®. This fenofibrate formulation is available in capsule form and contains 67 mg of micronized fenofibrate. Each capsule also contains lactose, pregelatinized starch, sodium lauryl sulfate, crospovidone and magnesium stearate. The bioavailability of fenofibrate is significantly improved over the non-micronized forms, thus reducing the daily maximum dose of fenofibrate in this formulation to 200 mg. However, it still requires administration of three capsules daily, which can result in patient inconvenience. Furthermore, the absorption of fenofibrate from Tricor® is heavily influenced by the presence of food, thus requiring Tricor® to be administered with meals to optimize bioavailability. The number of capsules per day, meal requirements and variability in bioavailability all present significant patient compliance challenges in the management of lipid disorders.

The preparation of fenofibrate in the form of crystalline microparticles or that of co-micronizing fenofibrate with a solid surfactant is a time consuming and costly process. An inherent drawback of micronization is that the material obtained must comply with stringent particle size specifications for quality and performance. In addition, processes that require the production of coating layers and inert matrixes are also complex, time consuming and costly. Furthermore, the handling and filling of capsules with a micronized powder present challenges with regard to safety and ensuring uniformity of the active agent throughout the formulation. Most importantly, a micronized microparticle or a co-micronized mixture containing fenofibrate requires complete and consistent dissolution of the drug as a prerequisite for the effective absorption of fenofibrate and to obtain a satisfactory bioavailability profile.

Other approaches for producing fenofibrate formulations have been described. U.S. Pat. No. 5,827,536 to Laruelle discloses a fenofibrate formulation containing fenofibrate in solution of a solubilizing agent consisting of a non-ionic surfactant, diethylene glycol monoethyl ether (DGME).

U.S. Pat. No. 5,545,628 to Deboeck et al. discloses pharmaceutical compositions for treating hyperlipidemia or hypercholesterolemia or both in a mammal. The compositions contain fenofibrate and an excipient containing one or more polyglycolyzed glycerides. The polyglycolzed glycerides are generally mixtures of known monoesters, diesters and triesters of glycerols and known monoesters and diesters of polyethylene glycol with a mean relative molecular mass between 200 and 6000. They may be obtained by partial transesterification of triglycerides with polyethylene glycol or by esterification of glycerol and polyethylene glycol with fatty acids.

U.S. Pat. No. 6,096,338 to Lacy et al. discloses a carrier for hydrophobic drugs, e.g., fenofibrate, that contains a digestible oil and a pharmaceutically acceptable surfactant for dispersing the oil in vivo upon administration of the carrier. The surfactant comprises a hydrophilic surfactant component which substantially inhibits the in vivo lipolysis of the digestible oil and a lipophilic surfactant component capable of at least substantially reducing the inhibitory effect of the hydrophilic surfactant component. The lipophilic surfactant component is present in an amount sufficient to achieve the required counteracting of the lipolysis-inhibiting properties of the hydrophilic surfactant component.

WO 99/29300A1 discloses a self-emulsifying preconcentrate containing fenofibrate dissolved in a carrier system comprising a hydrophobic component, a surfactant and a hydrophilic component. Each of these approaches, however, has individual drawbacks.

Therefore, for more effective and economic disease management, there is an ongoing need for improved fenofibrate formulations. In particular, there is a need for fenofibrate formulations that are not dependent on the micronization of fenofibrate or the co-nicronization of fenofibrate with a solid surfactant for effective absorption. Such formulations are more easily administered, e.g., administered without regard to meals (to enhance patient compliance), adequately bioavailable and less costly to manufacture and commercialize.

SUMMARY OF THE INVENTION

Accordingly, it is a primary object of the invention to address the above-mentioned need in the art by providing a pharmaceutical composition and dosage form for orally administering hydrophobic therapeutic agents, particularly fenofibrate.

It is another object of the invention to provide such a composition and dosage form comprising a therapeutically effective amount of fenofibrate and a solubilizer.

It is another object of the invention to provide such a composition and dosage form wherein the solubilizer comprises a vitamin E substance, a trialkyl citrate, a lactone, a nitrogen-containing solvent or a combination thereof.

It is still another object of the invention to provide such a composition and dosage form wherein the solubilizer comprises a phospholipid.

It is yet another object of the invention to provide such a composition and dosage form wherein the solubilizer comprises a glyceryl acetate, a fatty acid ester of an acetylated glyceride or a combination thereof.

It is a further object of the invention to provide such a composition and dosage form wherein the solubilizer comprises a lower alcohol fatty acid ester.

It is a further object of the invention to provide such a composition and dosage form wherein the solubilizer consists essentially of a lower alcohol fatty acid ester.

It is still another object of the invention to provide a composition and dosage form wherein the solubilizer consists essentially of a glycerol fatty acid ester.

It is yet another object of the invention to provide a composition and dosage form wherein the solubilizer consists essentially of a propylene glycol ester.

It is still another object of the invention to provide a composition and dosage form wherein the solubilizer consists essentially of an ethylene glycol ester.

It is yet another object of the invention to provide a composition and dosage form wherein the solubilizer consists essentially of a glycerol fatty acid ester, a propylene glycol ester, an ethylene glycol ester, a lower alcohol fatty acid ester or a combination thereof.

It is still another object of the invention to provide a pharmaceutical composition and dosage form comprising a therapeutically effective amount of a hydrophobic drug and a vitamin E substance.

It is yet another object of the invention to provide a method for treating a patient who would benefit from administration of a fenofibrate-containing composition comprising administering to the patient a therapeutically acceptable amount of the fenofibrate-containing compositions described herein.

Additional objects, advantages and novel features of the invention will be set forth in part in the description which follows, and in part will become apparent to those skilled in the art upon examination of the following, or may be learned by practice of the invention.

In one embodiment, then, the invention is directed to a pharmaceutical composition for oral administration of fenofibrate, wherein the composition comprises a therapeutically effective amount of fenofibrate and a solubilizer. The solubilizer is selected to effectively solubilize fenofibrate in the composition. Suitable solubilizers include, but are not limited to: a vitamin E substance such as vitamin E and derivatives thereof; monohydric alcohol esters such as trialkyl citrates, lactones and lower alcohol fatty acid esters; nitrogen-containing solvents; phospholipids; glycerol acetates such as acetin, diacetin and triacetin; glycerol fatty acid esters such as mono-, di- and triglycerides and acetylated mono- and diglycerides; propylene glycol esters; ethylene glycol esters; and combinations thereof.

The pharmaceutical compositions and dosage forms described herein may optionally comprise one or more additives. Preferred additives include surfactants and polymers. In addition, the composition is not limited with regard to its form, but it is preferred that the formulation is in liquid or semi-solid form. Furthermore, the fenofibrate in the aforementioned pharmaceutical composition may be completely solubilized or partially solubilized and partially suspended in the composition.

In another embodiment, a dosage form is provided comprising the aforementioned pharmaceutical composition. The dosage form contains a therapeutically effective amount of fenofibrate, preferably in an amount of about 40 to about 250 mg, and more preferably in an amount of about 67 to about 200 mg. The dosage form contains fenofibrate solubilized in the composition, preferably in an amount of at least about 40 mg, more preferably in an amount of at least about 67 mg, and most preferably in an amount of at least about 100 mg. Although the dosage form may be any suitable dosage form, the dosage form is preferably a capsule containing the pharmaceutical composition having a therapeutically effective amount of fenofibrate contained therein.

In still another embodiment, a pharmaceutical composition is provided comprising a therapeutically effective amount of a hydrophobic drug and a vitamin E substance. The hydrophobic drug is present in an amount of from about 0.1 to 30% w/w of the composition. Furthermore, the hydrophobic drug is at least about 50% solubilized in the composition. The vitamin E substance in the composition is present in an amount of from about 1 to 99% w/w of said composition.

In yet another embodiment, a method is provided for treating a patient who would benefit from administration of a fenofibrate-containing composition. The method comprises orally administering to the patient a therapeutically acceptable amount of the fenofibrate-containing compositions described herein.

DETAILED DESCRIPTION OF THE INVENTION

I. Definitions and Nomenclature

Before the present formulations and dosage forms are disclosed and described, it is to be understood that unless otherwise indicated this invention is not limited to specific dosage forms, solubilizers, or the like, as such may vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a solubilizer" includes a single solubilizer or mixtures of two or more solubilizers, reference to "an additive" refers to a single additive or mixtures of different additives, reference to "an additional active agent" includes a single additional active agent or combinations of two or more additional active agents, and the like.

In this specification and in the claims that follow, reference will be made to a number of terms which shall be defined to have the following meanings:

"Optional" or "optionally" means that the subsequently described circumstance may or may not occur, so that the description includes instances where the circumstance occurs and instances where it does not.

The terms "active agent," "drug" and "pharmacologically active agent" are used interchangeably herein to refer to a chemical material or compound which, when administered to an organism (human or animal, generally human) induces a desired pharmacologic effect. In the context of the present invention, the terms generally refer to a hydrophobic therapeutic active agent, preferably fenofibrate, unless the context clearly indicates otherwise.

By "pharmaceutically acceptable" is meant a carrier comprised of a material that is not biologically or otherwise undesirable.

"Carrier" or "vehicle" as used herein refer to carrier materials suitable for drug administration. Carriers and vehicles useful herein include any such materials known in the art, e.g., any liquid, gel, solvent, liquid diluent, solubilizer, surfactant, or the like, which is nontoxic and which does not interact with other components of the composition in a deleterious manner.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Thus, for example, "treating" a lipid disorder, as the term "treating" is used herein, encompasses both prevention of lipid disorders in a predisposed individual and treatment of lipid disorders in a clinically symptomatic individual.

"Patient" as used herein refers to a mammalian, preferably human, individual who can benefit from the pharmaceutical compositions and dosage forms of the present invention.

The term "vitamin E substance" refers to both vitamin E and derivatives thereof

By the terms "effective amount" or "therapeutically effective amount" of an agent as provided herein are meant a nontoxic but sufficient amount of the agent to provide the desired therapeutic effect. The exact amount required will vary from subject to subject, depending on the age, weight and general condition of the subject, the severity of the condition being treated, the judgment of the clinician, and the like. Thus, it is not possible to specify an exact "effective amount." However, an appropriate "effective amount" in any individual case may be determined by one of ordinary skill in the art using only routine experimentation.

The term "lipid disorder" refers to a condition wherein the level of one or more lipids in the blood of a patient deviates from normal. Thus, "lipid disorders" include above normal levels of lipids such as cholesterol (including low density lipoproteins), triglycerides and apolipoprotein B and below normal levels of lipids such as high density lipoproteins. When administered, the fenofibrate-containing compositions described herein are effective in treating patients suffering from a "lipid disorder" by reducing one or more lipid levels. Preferably, although not necessarily, each lipid level will return to a normal level.

II. The Pharmaceutical Composition

The pharmaceutical compositions described herein contain a hydrophobic therapeutic agent in substantially solubilized form. The compositions improve the bioavailability of the active agent after oral administration and/or improve patient compliance through an easily followed dosing regimen. The compositions described herein preferably contain the active agent, i.e., fenofibrate, in a substantially solubilized form and the effective absorption of the active agent is not dependent on the dissolution of crystalline material of the active agent.

In the art of pharmaceutical formulation, vitamin E substances have been known for their reducing potential and exclusively used as antioxidant in pharmaceutical compositions. The inventors have found, however, that vitamin E substances have unexpected solubilization power toward fenofibrate and other hydrophobic therapeutic agents.

The inventors also have surprisingly found that nitrogen-containing solvents have unexpected solubilization power toward fenofibrate and other hydrophobic therapeutic agents relative to other commonly used non-nitrogen containing solvents such as glycerol, propylene glycol, and polyethylene glycols. With additional research, the inventors have further surprisingly found that replacing one or more of the hydroxyl groups of glycerol and propylene glycol with, for example, a lower alkyl ester, results in a propylene glycol or glycerol fatty acid ester with an unexpectedly high solubilizing power for fenofibrate. Similarly, additional research has yielded other unexpectedly effective solubilizers for fenofibrate including esters of monohydric alcohols such as ethanol and ethylene glycols such as polyethylene glycols with an organic acid such as acetic acid, fatty acids and citric acids. In contrast to most conventional fenofibrate compositions, the present compositions do not require a separate step for the dissolution of crystalline fenofibrate since a significant fraction of fenofibrate is already solubilized in the compositions. In addition, the present compositions are not dependent on lipolysis for the absorption of fenofibrate since the compositions do not require triglycerides or vegetable oils.

A. Active Agent

The active agent in the present invention is generally hydrophobic in nature (log P greater than 2, P is the intrinsic octanol partition coefficient). Preferred classes of active agents from which the hydrophobic drug may be selected include the following: analgesics, anti-inflammatory agents, anti-helminthics, anti-arrhythmic agents, anti-asthma agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, immunosuppressants, anti-protozoal agents, anti-thyroid agents, anti-tussives, anxiolytics, sedatives, hypnotics, neuroleptics, β-blockers, cardic inotropic agents, cell adhesion inhibitors, corticosteroids, cytokine receptor activity modulators, diuretics, anti-parkinsonian agents, gastro-intestinal agents, histamine H-receptor antagonists, keratolytics, lipid regulating agents, muscle relaxants, nitrates and other anti-anginal agents, non-steroid anti-asthma agents, nutritional agents, opioid analgesics, sex hormones, stimulants and anti-erectile dysfunction agents.

A preferred class of hydrophobic drugs in the present invention is a lipid regulation agent such as a statin compound, a squalene synthesis inhibitor, a fibrate compound, a LDL (low density lipoprotein) catabolism enhancer or combinations thereof.

Statin compounds are drugs that lower blood cholesterol levels by inhibiting hydroxymethylglutalyl CoA (HMG-CoA) reductase. Examples of preferred statin compounds include pravastatin, simvastatin, lovastatin, atorvastatin, fluvastatin and salts thereof.

Squalene synthesis inhibitors are drugs that lower blood cholesterol levels by inhibiting the synthesis of squalene. An examples of a preferred squalene synthesis inhibitor includes (S)-alpha-Bis(2,2-dimethyl-1-oxopropoxy)methoxy-phosphinyl-3-phenoxybenzenebutanesulfonic acid mono potassium salt (BMS-188494).

Fibrate compounds are drugs that lower blood cholesterol levels by inhibiting the synthesis and secretion of triglycerides in the liver and activate a lipoprotein lipase. Examples of preferred fibrate compounds include bezafibrate, beclobrate, binifibrate, ciplofibrate, clinofibrate, clofibrate, clofibric acid, etofibrate, fenofibrate, fenofibric acid gemfibrozil, nicofibrate, pirifibrate, ronifibrate, simfibrate, theofibrate and combinations thereof.

LDL catabolism enhancers are drugs that lower blood cholesterol levels by increasing the number of LDL (low-density lipoprotein) receptors.

The above-mentioned statin compounds, squalene synthesis inhibitors, fibrate compounds and LDL catabolism enhancers can be substituted with other drugs that can lower blood cholesterol and triglyceride levels. Examples of these drugs include: nicotinic acid derivatives such as nicomol and niceritrol; antioxidants such as probucol; and ion-exchange resins such as cholestyramine and cholestipol.

A particularly preferred active agent in the present invention is fenofibrate. Fenofibrate is commercially available from Sigma®, St. Louis, Mo. (product number F6020). The pharmaceutical compositions and dosage forms contain a therapeutically effective amount of fenofibrate.

The absorption of fenofibrate in the composition is not dependent on the dissolution of fenofibrate from the composition in the patient's gastrointestinal tract since a substantial fraction of the fenofibrate in the composition itself is already solubilized. Thus, fenofibrate is not required to be micronized prior to incorporation in the composition. To the extent that fenofibrate is micronized in the present compositions, e.g., to further enhance solubility, it is preferred that the fenofibrate is micronized in the absence of any other components, particularly solid surfactants.

An additional active agent may be administered with the active agent included in the compositions and dosage forms of the present invention. It is preferred, however, that the additional active agent is contained within the composition and dosage form. It is particularly preferred that the active agent, i.e., primary active agent, and the additional active agent are both from the lipid regulating class. The weight ratio of the primary active agent to the additional active agent may be varied and will depend upon the effective dose of each ingredient. Each active agent contained in the composition or dosage form will be present in a therapeutically effective amount.

Additional active agents may be solubilized or suspended with or without the presence of an additional solubilizer. For those additional active agents that are ionized or ionizable, the formulations described herein may include a buffer to facilitate or maintain the presence of a preferred ionized form of the additional active agent in the formulation.

A wide range of additional active agents may be co-administered with fenofibrate including agents that bind cholesterol, e.g., cholestyramine, to synergistically treat certain lipid disorders. Other preferred additional active agents include acipimox, acifran, p-aminosalicylic acid, aspirin, atorvastatin, bezafibrate, cerivastatin, ciprofibrate, clinofibrate, clofibrate, colestipol, fluindostatin, fluvastatin, gemfibrozil, imanixil, istigmastanylphosphorylcholine, lipostabil, lovastatin, melinamide, mevastatin, neomycin, nicotinic acid, pravastatin, probucol, simvistatin, tetrahydrolipstatin, rapamycin, progesterone, estrodial, velostatin, captopril, pivopril, enalopril, fosinopril, ramipril, cetapril, cilazapril, delapril, indolapril, spirapril, quinapril and mixtures thereof.

Other examples of the additional active agents include: insulin sensitivity enhancers, insulin secretion enhancers and/or an insulin preparation; an alpha-glucosidase inhibitor; an aldose reductase inhibitor; a biguanide; and an angiotensin converting enzyme inhibitor. Insulin sensitivity enhancers are agents that substantially increase insulin sensitivity in muscle, liver and adipose tissue resulting in the correction of elevated plasma levels of glucose, triglycerides and nonesterified fatty acids without the occurrence of hypoglycemia. Examples of insulin sensitivity enhancers include, but are not limited to the glitazones (thiazolidinediones such as pioglitazone, troglitazone, rosiglitazone, MCC-555, and BRL49653).

Insulin secretion enhancers are drugs that promote the secretion of insulin from pancreatic beta-cells. The group of drugs known as sulfonylureas represents a preferred class of insulin secretion enhancers. The sulfonylureas are drugs that promote the secretion of insulin from pancreatic beta-cells by transmitting signals of insulin secretion via sulfonylurea receptors in cell membranes. Examples of the sulfonylureas include, but are not limited to: tolbutamide; chlorpropamide; tolazamide; acetohexamide; 4-chloro-N (1-pyrolidinylamino)carbonyl-benzenesulfonamide (generic name: glycopyramide) or its ammonium salt; glibenclamide (glyburide); gliclazide; 1-butyl-3-metanilylurea; carbutamide; glibonuride; glipizide; gliquidone; glisoxepid; glybuthiazole; glibuzole; glyhexamide; glymidine; glypinamide; phenbutamide; tolcyclamide and combinations thereof.

Other insulin secretion enhancers include N-(4-(1-methylethyl)cyclohexyl)carbonyl-D-phenylalanine (AY-4166), calcium(2S)-2-benzyl-3-(cis-hexahydro-2-isoindolinylcarbonyl)propionate dihydrate (KAD-1229), and glimepiride (Hoe 490). The insulin secretion enhancer is especially preferably glibenclamide.

Examples of the insulin preparations include animal insulin preparations typically extracted from bovine or porcine pancreas and human insulin preparations synthesized by genetic engineering techniques typically using *Escherichia coli* or yeasts. Each of these types of insulin is readily available commercially from, for example, Eli Lilly and Co., Indianapolis, Ind. While insulin preparations are available in a variety of types, e.g. immediate-acting, bimodal-acting, intermediate-acting, and long-acting, these types of preparations can be selectively administered according to the patient's condition.

α-Glucosidase inhibitors are drugs that inhibit digestive enzymes such as amylase, maltase, α-dextrinase, sucrase, etc. to retard digestion of starch and sugars. Examples preferred α-glucosidase inhibitors include acarbose, N-(1, 3-dihydroxy-2-propyl)valiolamine (generic name; voglibose), miglitol and combinations thereof. Voglibose is a particularly preferred α-glucosidase inhibitor.

Aldose reductase inhibitors are drugs that inhibit the first-stage rate-limiting enzyme in the polyol pathway to prevent or arrest diabetic complications. In the hyperglycemic state of diabetes, the utilization of glucose in the polyol pathway is increased and the excess sorbitol accumulated intracellularly acts as a tissue toxin. The toxicity triggers the onset of complications such as diabetic neuropathy, retinopathy and nephropathy. Examples of aldose reductase inhibitors include, but are not limited to, tolurestat; epalrestat, imirestat, zenarestat, zopolrestat, sorbinil; 1-(3-bromo-2-benzofuranyl)sulfonyl-2,4-imidazolidinedione (M-16209) and combinations thereof.

Biguanides are drugs that stimulate anaerobic glycolysis, increase the sensitivity to insulin in the peripheral tissues, inhibit glucose absorption from the intestine, suppress hepatic gluconeogenesis, and inhibit fatty acid oxidation. Examples of the biguanides include, but are not limited to phenformin, metformin, buformin and combinations thereof.

Angiotensin converting enzyme inhibitors are drugs that partially lower blood glucose levels in addition to lowering blood pressure by inhibiting angiotensin converting enzymes. Examples of angiotensin converting enzyme inhibitors include, for example, captopril, enalapril, alacepril, delapril, ramipril, lisinopril, imidapril, benazepril, ceronapril, cilazapril, enalaprilat, fosinopril, moveltopril, perindopril, quinapril, spirapril, temocapril, trandolapril and combinations thereof.

B. Solubilizer

In addition to fenofibrate, the pharmaceutical compositions of the invention also contain a carrier. At a minimum, the carrier must contain a solubilizer. In some instances, the carrier may only contain one solubilizer without any additional components, i.e., additives. Alternatively, the carrier may contain one or more pharmaceutically acceptable additives in addition to the solubilizer.

In the context of the present invention, a solubilizer is any material that has a solubility for fenofibrate of at least about 45 mg per gram of the solubilizer, more preferably at least about 67 mg per gram of the solubilizer and most preferably at least about 100 mg per gram of the solubilizer. The solubilizer is preferably present in an amount such that a significant fraction of fenofibrate is solubilized in the composition and is capable of providing an immediate and therapeutically effective amount of fenofibrate to a patient in a readily absorbable form upon administration. As a consequence of the solubilizer in the composition, micronization of fenofibrate or the co-micronization of fenofibrate with a solid surfactant is not necessary in order to achieve pharmaceutically acceptable compositions. Preferably, the solubilizers of the present invention can also increase the solubilization of fenofibrate when the composition contacts an aqueous medium including water, and particularly gastrointestinal fluids upon administration of the dosage form containing the composition. Thus, the solubilizers as provided herein improve the dissolution profile of fenofibrate and thereby the bioavailability of fenofibrate.

One type of solubilizer that may be used is a vitamin E substance. This group of solubilizers includes a substance belonging to the group of α-, β-, γ-, δ-, $\zeta_1$-, $\zeta_2$- and η-tocopherols, their dl, d and l forms and their structural analogues, such as tocotrienols; the corresponding derivatives, e.g., esters, produced with organic acids; and mixtures thereof. As will be appreciated by those of skill in the art, only those vitamin E substances that effectively solubilize fenofibrate may be included in the present compositions as solubilizers. One skilled in the art can easily identify vitamin E substances that may serve as effective solubilizers by, for example, mixing a particular vitamin E substance with fenofibrate and determining the extent of solubility. Preferred vitamin E substance solubilizers include tocopherols, tocotrienols and tocopherol derivatives with organic acids such as acetic acid, propionic acid, bile acid, lactic acid, pyruvic acid, oxalic acid, malic acid, malonic acid, succinic acid, maleic acid, fumaric acid, tartaric acid, citric acid, benzoic acid, cinnamic acid, mandelic acid, polyethylene glycol succinate and salicylic acid. Particularly preferred vitamin E substances include alpha-tocopherol, alpha-tocopheryl acetate, alpha-tocopheryl acid succinate, alpha-tocopheryl polyethylene glycol 1000 succinate and mixtures thereof.

Another group of solubilizers are monohydric alcohol esters of organic acids. The monohydric alcohol can be, for example, ethanol, isopropanol, t-butanol, a fatty alcohol, phenol, cresol, benzyl alcohol or a cycloalkyl alcohol. The organic acid can be, for example, acetic acid, propionic acid, butyric acid, a fatty acid of 6–22 carbon atoms, bile acid, lactic acid, pyruvic acid, oxalic acid, malic acid, malonic acid, succinic acid, maleic acid, fumaric acid, tartaric acid, citric acid, benzoic acid, cinnamic acid, mandelic acid and salicylic acid. Preferred solubilizers in this group include trialkyl citrates, lower alcohol fatty acid esters and lactones. Preferred trialkyl citrates include triethyl citrate, acetyltriethyl citrate, tributyl citrate, acetyltributyl citrate and mixtures thereof with triethyl citrate being particularly preferred. Lower alcohol fatty acid esters, as the name implies, comprise a lower alcohol moiety, i.e., containing 2–4 carbon atoms, and a fatty acid moiety of about 6–22 carbon atoms. Particularly preferred lower alcohol fatty acid esters include ethyl oleate, ethyl linoleate, ethyl caprylate, ethyl caprate, isopropyl myristate, isopropyl palmitate and mixtures thereof. Lactones may also serve as a solubilizer. Examples include ε-caprolactone, δ-valerolactone, β-butyrolactone, isomers thereof and mixtures thereof.

The solubilizer may be a nitrogen-containing solvent. Preferred nitrogen-containing solvents include dimethylformamide, dimethylacetamide, N-alkylpyrrolidone, N-hydroxyalkylpyrrolidone, N-alkylpiperidone, N-alkylcaprolactam and mixtures thereof wherein alkyl is a $C_{1-12}$ branched or straight chain alkyl. Particularly preferred nitrogen-containing solvents include N-methyl 2-pyrrolidone, N-ethyl 2-pyrrolidone or a mixture thereof. Alternatively, the nitrogen-containing solvent may be in the form of a polymer such as polyvinylpyrrolidone.

Another group of solubilizers includes phospholipids. Preferred phospholipids include phosphatidylcholine, phosphatidylethanolamine, phosphatidylserine, phosphatidylinositol, lecithins, lysolecithins, lysophosphatidylcholine, polyethylene glycolated phospholipids/lysophospholipids, lecithins/lysolecithins and mixtures thereof.

Another group of preferred solubilizers are glycerol acetates and acetylated glycerol fatty acid esters. Preferred glycerol acetates include acetin, diacetin, triacetin and mixtures thereof, with triacetin being particularly preferred. Preferred acetylated glycerol fatty acid esters include acetylated monoglycerides, acetylated diglycerides and mixtures thereof. In a most preferred embodiment, the acetylated monoglyceride is a distilled acetylated monoglyceride.

In addition, the solubilizer may be a glycerol fatty acid ester. The fatty acid component is about 6–22 carbon atoms. The glycerol fatty acid ester can be a monoglyceride, diglyceride, triglyceride or mixtures thereof. Preferred glycerol fatty acid esters include monoglycerides, diglycerides, medium chain triglycerides with fatty acids having about 6–12 carbons and mixtures thereof. Particularly preferred glycerol fatty acid esters include medium chain monoglycerides with fatty acids having about 6–12 carbons, medium chain diglycerides with fatty acids having about 6–12 carbons and mixtures thereof.

The solubilizer may be a propylene glycol ester. Preferred propylene glycol esters include propylene carbonate, propylene glycol monoacetate, propylene glycol diacetate, propylene glycol fatty acid esters, acetylated propylene glycol fatty acid esters and mixtures thereof. Alternatively, the propylene glycol fatty acid ester may be a propylene glycol fatty acid monoester, propylene glycol fatty acid diester or mixture thereof. The fatty acid has about 6–22 carbon atoms. It is particularly preferred that the propylene glycol ester is propylene glycol monocaprylate. Other preferred propylene glycol esters include propylene glycol dicaprylate, propylene glycol dicaprate, propylene glycol dicaprylate/dicaprate and mixtures thereof.

Another group of solubilizers are ethylene glycol esters. Ethylene glycol esters include monoethylene glycol monoacetates, diethylene glycol esters, polyethylene glycol esters and mixtures thereof. Additional examples include ethylene glycol monoacetates, ethylene glycol diacetates, ethylene glycol fatty acid monoesters, ethylene glycol fatty acid diesters, and mixtures thereof. Alternatively, the ethylene glycol ester may be a polyethylene glycol fatty acid monoesters, polyethylene glycol fatty acid diesters or mixtures thereof. Again, the fatty acid component will contain about 6–22 carbon atoms. Particularly preferred ethylene glycol esters are those obtained from the transesterification of polyethylene glycol with a triglyceride or a vegetable oil or mixture thereof and include, for example, those marketed under the Labrafil® and Labrasol® names.

C. Additives

Although not always necessary, the compositions of the present invention may also include one or more additional components, i.e., additives. When present, however, the additional components do not act as solubilizers per se, but rather as an adjuvant to facilitate the formation and maintenance of a pharmaceutically acceptable composition. Classes of additives that may be present in the compositions, include, but are not limited to, absorbents, acids, adjuvants, anticaking agent, glidants, antitacking agents, antifoamers, anticoagulants, antimicrobials, antioxidants, antiphlogistics, astringents, antiseptics, bases, binders, chelating agents, sequestrants, coagulants, coating agents, colorants, dyes, pigments, compatiblizers, complexing agents, softeners, crystal growth regulators, denaturants, dessicants, drying agents, dehydrating agents, diluents, dispersants, emollients, emulsifiers, encapsulants, enzymes, fillers, extenders, flavor masking agents, flavorants, fragrances, gelling agents, hardeners, stiffening agents, humectants, lubricants, moisturizers, bufferants, pH control agents, plasticizers, soothing agents, demulcents, retarding agents, spreading agents, stabilizers, suspending agents, sweeteners, disintegrants, thickening agents, consistency regulators, surfactants, opacifiers, polymers, preservatives, antigellants, rheology control agents, UV absorbers, tonicifiers and viscomodulators. One or more additives from any particular class, as well as one or more different classes of additives, may be present in the compositions. Specific examples of additives are well known in the art.

III. Determination of Component Amounts and Preparation of Compositions

As will be recognized by those skilled in the art, the amount or percentage of the active agent present in the composition and dosage forms will vary. Thus, for example, the amount of active agent is based, in part, upon the actual need of the patient and can be determined by the attending clinician. In all cases, however, the amount of the active agent present in the composition and dosage forms is an amount such that the active agent is significantly solubilized in the appropriately selected solubilizer or solubilizers so that the aforementioned advantages of the present invention are achieved.

Preferably, the compositions are formulated so as to contain a sufficient amount, i.e., dose, of fenofibrate within a dosage unit, e.g., a capsule. It is preferred that the amount of fenofibrate will be present in the composition so as to provide each dosage form with a unit dosage of from about 40 to about 250 mg, and preferably about 67 to about 200 mg of fenofibrate. It is particularly preferred that the entire amount of fenofibrate is solubilized in the composition. However, it is sometimes necessary to add additional fenofibrate in non-solubilized form when the fenofibrate solubility capacity of a given composition is exceeded. Therefore, it is also an important feature of the present invention that the fenofibrate present in the composition is significantly solubilized. Typically, at least about 50% of the fenofibrate is solubilized in the composition and preferably at least about 75% of the fenofibrate is solubilized in the composition of the dosage form. The dosage form contains fenofibrate solubilized in the composition in an amount of at least about 40 mg, preferably in an amount of at least about 67 mg, and more preferably in an amount of at least about 100 mg.

The amount of solubilizer that can be included in the dosage forms of the present invention is not particularly limited. When the dosage forms are ultimately administered to a patient, however, the amount of any given solubilizer is limited to a bioacceptable amount. Bioacceptable amounts of solubilizers and other components are readily determined by one of skill in the art by using routine experimentation or searching the literature. In some circumstances, it may be advantageous to include amounts of solubilizers far in excess of bioacceptable amounts, for example, to maximize the concentration of the fenofibrate, with excess solubilizer removed prior to providing the composition to a patient. Excess solubilizer may be removed using conventional techniques such as distillation, spray drying, lyophilization or evaporation. Generally, the amount of solubilizer in the composition will be from about 5 wt. % to about 95 wt. %, preferably between about 20 wt. % to about 70 wt. %.

The amount of additional components in the compositions can be determined by one of ordinary skill in the art, according to the desired property or properties to be imparted to the composition. For example, the amount of a suspending agent may be determined by adding gradual amounts of the agent until the desired homogeneity of undissolved drug particles in the composition is achieved. For a colorant, the amount of the colorant may determined by adding small amounts of the colorant until the desired color of the composition is achieved. For a surfactant, the amount of a surfactant may determined by adding gradual amounts of the surfactant until the desired wetting effect or dispersibility of the composition is achieved. The amount of surfactant, when present, in the composition will generally be up to about 80 wt. %, preferably between about 10 wt. % to about 50 wt. %.

The pharmaceutical compositions of the present invention are prepared by conventional methods well known to those skilled in the art. The composition can be prepared by mixing the active agent, the solubilizer, and optional additive according to methods well known in the art. Excess solvent or solubilizer, added to facilitate solubilization of the active agent and/or mixing of the formulation components, can be removed before administration of the pharmaceutical dosage form. The compositions can be further processed according to conventional processes known to those skilled in the art, such as lyophilization, encapsulation, compression, melting, extrusion, balling, drying, chilling, molding, spraying, spray congealing, coating, comminution, mixing, homogenization, sonication, cryopelletization, spheronization and granulation to produce the desired dosage form.

For dosage forms substantially free of water, i.e., when the composition is provided in a pre-concentrated form for administration or for later dispersion in an aqueous system, the composition is prepared by simple mixing of the components to form a pre-concentrate. The compositions comprising solubilized fenofibrate can be further formulated into desirable dosage forms utilizing skills well known in the art. For example, compositions in liquid or semi-solid form can be filled into soft gelatin capsules using appropriate filling machines. Alternatively, the composition can also be sprayed, s granulated or coated onto a substrate to become a powder, granule or bead that can be further encapsulated or tableted if the compositions solidify at room temperature with or without the addition of appropriate solidifying or binding agents. This approach allows for the creation of a "fused mixture," a "solid solution" or a "eutectic mixture."

As previously indicated, the compositions may include additional amounts of fenofibrate over the amount that is solubilized in the composition. In such a case, fenofibrate can be partially suspended in the composition in any desired crystalline or amorphous form. Such partially solubilized and partially suspended fenofibrate compositions can be prepared by adding solids of fenofibrate of desired form and particle size. For example, micronized crystalline fenofibrate having an average particle size of less than 30 microns, nanosized crystalline fenofibrate having an average particle size of less than 1 micron or meshed amorphous fenofibrate may be added to the composition. Such micronized or nanosized fenofibrate particles can be obtained by precipitation or size reduction techniques well-known in the art. In addition, partially suspended fenofibrate compositions may be obtained from a supersaturated fenofibrate solution or by co-precipitation with an additive from a fenofibrate solution.

IV. Dosage Forms

In a preferred embodiment, the pharmaceutical composition is present in a single dosage form. The dosage form(s) are not limited with respect to size, shape or general configuration, and may comprise, for example, a capsule, a tablet or a caplet, or a plurality of granules, beads, powders or pellets that may or may not be encapsulated. In addition, the dosage form may be a drink or beverage solution or a spray solution that is administered orally. Thus, for example, the drink or beverage solution may be formed by adding a therapeutically effective amount of the composition in, for example, a powder or liquid form, to a suitable beverage, e.g., water or juice.

A preferred dosage form is a capsule containing a composition as described herein. The capsule material may be either hard or soft and is generally made of a suitable compound such as gelatin, starch or a cellulosic material. As is known in the art, use of soft gelatin capsules places a number of limitations on the compositions that can be encapsulated. See, for example, Ebert (1978), "Soft Elastic Gelatin Capsules: A Unique Dosage Form," *Pharmaceutical Technology* 1(5). Two-piece hard gelatin capsules are preferably sealed, such as with gelatin bands or the like. See, for example, *Remington: The Science and Practice of Pharmacy*, Nineteenth Edition. (1995) cited supra, which describes materials and methods for preparing encapsulated pharmaceuticals. In this embodiment, the encapsulated composition may be liquid or semi-solid (e.g., a gel).

V. Utility and Administration

In accordance with the present invention, the pharmaceutical compositions and dosage forms can be administered to treat patients. For example, the fenofibrate-containing compositions and dosage forms described herein can be administered to patients who would benefit from fenofibrate therapy. Patients suffering from any condition, disease or disorder which can be effectively treated with fenofibrate can benefit from the administration of a therapeutically effective amount of the fenofibrate-containing compositions described herein. In particular, however, the fenofibrate-containing compositions are effective inktreating lipid disorders.

Dosage regimens and daily dosages for fenofibrate can vary, as a number of factors are involved, including the particular condition or severity of the lipid disorder, the presence of renal and/or hepatic dysfunction and the age and general condition of the patient. It is necessary that the dose administered be sufficient to provide the desired pharmacological activity. Typical dosages for fenofibrate are on the order of about 40 to about 250 mg/day, generally in the range of about 67 to about 200 mg/day. The compositions and dosage forms are useful in treating lipid disorders.

The composition may be administered in the form of a capsule wherein a patient swallows the entire capsule. Alternatively, the composition may be contained in capsule which is then opened and mixed with an appropriate amount of aqueous fluid such as water or juice to form a drink or beverage for administration of the composition. As will be appreciated, the composition need not be contained in a capsule and may be housed in any suitable container, e.g., packets, ampules, etc. Once prepared, the drink or beverage is imbibed in its entirety thus effecting administration of the composition. Preparation of the composition-containing drink or beverage may be effected by the patient or by another, e.g., a caregiver. As will be appreciated by those skilled in the art, additional modes of administration are available.

It is to be understood that while the invention has been described in conjunction with the preferred specific embodiments thereof, that the description above as well as the examples which follow are intended to illustrate and not limit the scope of the invention. Other aspects, advantages and modifications within the scope of the invention will be apparent to those skilled in the art to which the invention pertains.

All patents, patent applications, and publications mentioned herein, both supra and infra, are hereby incorporated by reference.

Experimental

The practice of the present invention will employ, unless otherwise indicated, conventional techniques of pharmaceutical formulation, medicinal chemistry, and the like, which are within the skill of the art. Such techniques are explained fully in the literature. Preparation of various types of pharmaceutical formulations are described, for example, in *Remington: The Science and Practice of Pharmacy*, Nineteenth Edition. (1995) cited supra and Ansel et al., *Pharmaceutical Dosage Forms and Drug Delivery Systems*, 6<sup>th</sup> Ed. (Media, Pa.: Williams & Wilkins, 1995).

In the following examples, efforts have been made to ensure accuracy with respect to numbers used (e.g., amounts, temperature, etc.) but some experimental error and deviation should be accounted for. Unless indicated otherwise, temperature is in degrees C and pressure is at or near atmospheric. All components were obtained commercially unless otherwise indicated. "Tweene®" and "Arlacel®" components are available from ICI Americas, Wilmington, Del. "Cremophor®" components are available from BASF Corp., Mount Olive, N.J. "Imwitor®" and "Miglyol®" components are available from Hüls AG, Herne, Germany. "Lauroglycol®," "Labrafil®," "Labrasol®," "Transcutol®," "Maisine®" and "Capryol®" components are available from Gattefossé SA, Saint Priest, France. "Eastman®" components are available from Eastman Chemical Products, Inc., Kingsport, Tenn. "Captex®," and "Capmul®" components are available from Karlshamns USA, Inc., Columbus, Ohio. "Incrocas" and "Crovol" components are available from Croda, Inc., Parsippany, N.J.

In examples 1–7, the solubility of fenofibrate in various solubilizers was determined using conventional techniques such as incrementally adding fenofibrate until the solubilizer could no longer solubilize additional fenofibrate.

EXAMPLE 1

Solubility of Fenofibrate in Propylene Glycol and Propylene Glycol Esters

| Solubilizer | Solubility (mg/g) |
|---|---|
| Propylene Glycol | ~5 |
| Propylene Carbonate | 134–150 |
| Propylene glycol monocaprylate (Capryol ® 90) | 150–160 |
| Propylene glycol laurate (Lauroglycol ® FCC) | 100–108 |
| Propylene glycol dicaprylate/caprate (Miglyol ® 840) | 136–150 |

EXAMPLE 2

Solubility of Fenofibrate in Glycerol, Glycerol Acetate, and Acetylated Glycerol Esters

| Solubilizer | Solubility (mg/g) |
|---|---|
| Glycerol | <2 |
| Triacetin | 100–120 |
| Distilled acetylated monoglyceride (Eastman ® 9-45) | 136–150 |

EXAMPLE 3

Solubility of Fenofibrate in Glycerol and Glycerol Fatty Acid Esters

| Solubilizer | Solubility (mg/g) |
|---|---|
| Glycerol | <2 |
| Glycerol monooleate (Arlacel ® 186) | 45–50 |
| Glycerol mono-, dicaprylate (Imwitor ® 988) | 80–100 |
| Glycerol mono-, dicaprylate/caprate (Capmul ® MCM) | 67–80 |
| Gycerol tricaprylate/caprate (Miglyol ® 812) | 80–100 |
| Glycerol tricaprylate/caprate/linoleate (Miglyol ® 818) | 80–100 |
| Olive Oil | 40–50 |
| Corn Oil | 50–60 |
| Safflower Oil | 50–60 |

EXAMPLE 4

Solubility of Fenofibrate in Polyethylene Glycols and Polyethylene Glycol Fatty Acid Esters Including Transesterification Products of Polyethylene Glycol with Triglyceride/Vegetable Oil

| Solubilizer | Solubility (mg/g) |
|---|---|
| Polyethylene glycol 200 | 25–33 |
| PEG-8 monooleate | 100–110 |
| PEG-8 dioleate | 100–110 |
| PEG-8 dilaurate | 127–140 |
| PEG-6 corn oil (Labrafil ® M2125 CS) | 75–80 |
| PEG-6 apricot kernel oil (Labrafil ® M1944 CS) | 70–80 |
| PEG-8 caprylic/capric glycerides (Labrasol ®) | 100–110 |

EXAMPLE 5

Solubility of Fenofibrate in Esters of Organic Acid and Alcohol

| Solubilizer | Solubility (mg/g) |
|---|---|
| Triethyl Citrate | 140–150 |
| Ethyl Oleate | 100–108 |

EXAMPLE 6

Solubility of Fenofibrate in Vitamin E and Vitamin E Derivative

| Solubilizer | Solubility (mg/g) |
|---|---|
| dl-alpha-tocopherol | 175–200 |
| d-alpha-tocopheryl acetate | 90–100 |

EXAMPLE 7

Solubility of Fenofibrate in Nitrogen-Containing Solubitizers

| Solubilizer | Solubility (mg/g) |
|---|---|
| Dimethylacetamide | 900–1000 |
| Dimethylformamide | 830–900 |
| N-methyl 2-pyrrolidone | 750–800 |
| N-ethyl 2-pyrrolidone | 830–900 |

EXAMPLES 8–34

Compositions Comprising Fenofibrate

Compositions comprising fenofibrate in the examples were prepared by weighing out the components in the described amount, placing the components into an appropriate container, mixing the components in an appropriate manner and, if necessary, heating to facilitate the solubilization of fenofibrate in the compositions. The compositions can be .prepared by adding the components in any order. For example, fenofibrate can be added to an individual component or into mixtures of two or more components. The composition can be prepared at room temperature or gently heated to 40–60 ° C. The composition can also be prepared by melting fenofibrate at a temperature above the melting point, i.e., 79–82 ° C., followed by mixing it with other components. Traditional mixing techniques can be used including, for example, mechanical agitation, stirring and sonication of the components.

EXAMPLE 8

| Component | Amount (mg) |
|---|---|
| Fenofibrate | 67 |
| Triacetin | 700 |

EXAMPLE 9

| Component | Amount (mg) |
|---|---|
| Fenofibrate | 67 |
| Capryol ® 90 | 400 |
| Incrocas 35 | 400 |

EXAMPLE 10

| Component | Amount (mg) |
|---|---|
| Fenofibrate | 100 |
| Incrocas 35 | 500 |
| Transcutol ® | 500 |

EXAMPLE 11

| Component | Amount (mg) |
|---|---|
| Fenofibrate | 200 |
| Incrocas 35 | 400 |
| Capryol ® 90 | 400 |
| Transcutol ® | 400 |

EXAMPLE 12

| | Amount (mg) |
|---|---|
| Fenofibrate | 67 |
| Tween ® 80 | 200 |
| Eastman ® 9-45 | 300 |
| Triethyl Citrate | 150 |

EXAMPLE 13

| Component | Amount (mg) |
|---|---|
| Fenofibrate | 100 |
| Tween ® 80 | 300 |
| Eastman ® 9-45 | 500 |
| Triethyl Citrate | 200 |

EXAMPLE 14

| Component | Amount (mg) |
|---|---|
| Fenofibrate | 67 |
| Incrocas 35 | 500 |
| Eastman ® 9-45 | 400 |
| Triethyl Citrate | 100 |

EXAMPLE 15

| Component | Amount (mg) |
|---|---|
| Fenofibrate | 200 |
| Labrasol ® | 400 |
| Glycofurol | 400 |

EXAMPLE 16

| Component | Amount (mg) |
|---|---|
| Fenofibrate | 100 |
| Incrocas 35 | 300 |
| Capryol ® 90 | 300 |
| Miglyol ® 840 | 300 |

EXAMPLE 17

| Component | Amount (mg) |
|---|---|
| Fenofibrate | 200 |
| Olive Oil | 600 |
| Triethyl Citrate | 400 |

EXAMPLE 18

| Component | Amount (mg) |
|---|---|
| Fenofibrate | 67 |
| Labrafil ® M1944 CS | 400 |
| Safflower Oil | 380 |

EXAMPLE 19

| Component | Amount (mg) |
|---|---|
| Fenofibrate | 67 |
| Labrafil ® M2125 CS | 400 |
| Corn Oil | 380 |
| Ethanol | 120 |

EXAMPLE 20

| Component | Amount (mg) |
| --- | --- |
| Fenofibrate | 67 |
| Cremophor ® RH40 | 440 |
| Maisine ® I-35 | 400 |
| dl-alpha-tocopherol | 60 |
| Ethanol | 100 |

EXAMPLE 21

| Component | Amount (mg) |
| --- | --- |
| Fenofibrate | 100 |
| PEG-8 dilaurate | 500 |
| PEG 400 | 400 |

EXAMPLE 22

| Component | Amount (mg) |
| --- | --- |
| Fenofibrate | 67 |
| Tween ® 80 | 300 |
| Isopropyl Myristate | 500 |
| Ethanol | 100 |

EXAMPLE 23

| Component | Amount (mg) |
| --- | --- |
| Fenofibrate | 100 |
| Tween ® 80 | 240 |
| Ethyl Oleate | 400 |
| Ethanol | 80 |

EXAMPLE 24

| Component | Amount (mg) |
| --- | --- |
| Fenofibrate | 200 |
| dl-alpha-tocopherol | 1000 |

EXAMPLE 25

| Component | Amount (mg) |
| --- | --- |
| Fenofibrate | 40 |
| dl-alpha-tocopherol | 600 |
| Vitamin E-TPGS | 200 |

EXAMPLE 26

| Component | Amount (mg) |
| --- | --- |
| Fenofibrate | 67 |
| dl-alpha-tocopherol | 600 |
| Vitamin E-TPGS | 300 |
| Triethyl Citrate | 100 |

EXAMPLE 27

| Component | Amount (mg) |
| --- | --- |
| Fenofibrate | 67 |
| dl-alpha-tocopherol | 400 |
| Vitamin E-TPGS | 200 |

EXAMPLE 27-continued

| Component | Amount (mg) |
| --- | --- |
| Tween ® 80 | 200 |
| Triethyl Citrate | 200 |

EXAMPLE 28

| Component | Amount (mg) |
| --- | --- |
| Fenofibrate | 67 |
| dl-alpha-tocopherol | 400 |
| Labrafil ® M1944 CS | 400 |

EXAMPLE 29

| Component | Amount (mg) |
| --- | --- |
| Fenofibrate | 67 |
| dl-alpha-tocopherol | 500 |
| Crovol M40 | 300 |
| PEG 600 | 200 |

EXAMPLE 30

| Component | Amount (mg) |
| --- | --- |
| Fenofibrate | 67 |
| dl-alpha-tocopherol | 200 |
| Crovol M40 | 200 |
| Incrocas 35 | 400 |

EXAMPLE 31

| Component | Amount (mg) |
| --- | --- |
| Fenofibrate | 100 |
| dl-alpha-tocopherol | 260 |
| Soybean Oil | 80 |
| Imwitor ® 988 | 100 |
| Crovol M40 | 100 |
| Incrocas 35 | 460 |

EXAMPLE 32

| Component | Amount (mg) |
| --- | --- |
| Fenofibrate | 67 |
| dl-alpha-tocopherol | 400 |
| Captex ® 300 | 60 |
| Capmul ® MCM | 100 |
| Labrafil ® M2125 CS | 100 |
| Cremophor ® RH40 | 340 |

EXAMPLE 33

| Component | Amount (mg) |
| --- | --- |
| Fenofibrate | 67 |
| dl-alpha-tocopherol acetate | 500 |
| Triacetin | 150 |

EXAMPLE 34

| Component | Amount (mg) |
| --- | --- |
| Fenofibrate | 67 |
| dl-alpha-tocopherol acetate | 500 |
| Labrasol ® | 200 |
| Labrafil ® M1944 CS | 100 |

What is claimed is:

1. A pharmaceutical composition for oral administration of fenofibrate, comprising:
  a) a therapeutically effective amount of fenofibrate; and
  b) an effective solubilizing amount of a solubilizer selected from the group consisting of: a trialkyl citrate; a lactone; a combination of a trialkyl citrate and a lactone; a combination of a vitamin E substance and at least one of a trialkyl citrate and a lactone, and a combination of a nitrogen-containing solvent and at least one of a trialkyl citrate and a lactone.

2. The pharmaceutical composition of claim 1, wherein said solubilizer is a trialkyl citrate.

3. The pharmaceutical composition of claim 2, wherein said trialkyl citrate is selected from the group consisting of triethyl citrate, acetyltriethyl citrate, tributyl citrate, acetyltributyl citrate and mixtures thereof.

4. The pharmaceutical composition of claim 3, wherein said trialkyl citrate is triethyl citrate.

5. The pharmaceutical composition of claim 1, wherein said solubilizer is a lactone.

6. The pharmaceutical composition of claim 5, wherein said lactone is selected from the group consisting of ε-caprolactone and isomers thereof, δ-valerolactone and isomers thereof and β-butyrolactone and isomers thereof and mixtures thereof.

7. The pharmaceutical composition of claim 1, wherein said solubilizer comprises a mixture of a nitrogen-containing solvent and at least one of a trialkyl citrate and a lactone.

8. The pharmaceutical composition of claim 7, wherein said nitrogen-containing solvent is selected from the group consisting of dimethylformamide, dimethylacetamide, N-alkylpyrrolidone, N-hydroxyalkylpyrrolidone, N-alkylpiperidone, N-alkylcaprolactam and mixtures thereof.

9. The pharmaceutical composition of claim 7, wherein said nitrogen-containing solvent is selected from the group consisting of N-methyl 2-pyrrolidone, N-ethyl 2-pyrrolidone and mixtures thereof.

10. A method for treating a patient suffering from a lipid disorder, comprising administering to the patient a therapeutically effective amount of the composition of claim 1.

11. The pharmaceutical composition of claim 1, wherein the fenofibrate is at least 50% solubilized in the composition.

12. The pharmaceutical composition of claim 11, wherein the fenofibrate is at least 75% solubilized in the composition.

13. The pharmaceutical composition of claim 12, wherein the fenofibrate is completely solubilized in the composition.

14. The pharmaceutical composition of claim 1, in a liquid form.

15. The pharmaceutical composition of claim 1, in a semi-solid form.

16. A pharmaceutical dosage form comprising the pharmaceutical composition of claim 7.

17. The pharmaceutical dosage form of claim 16, comprising a unit dosage form.

18. The pharmaceutical dosage form of claim 17, comprising about 40 mg to about 250 mg fenofibrate.

19. The pharmaceutical dosage form of claim 18, comprising about 67 mg to about 200 mg fenofibrate.

20. The pharmaceutical dosage form of claim 16, in capsule form.

21. The pharmaceutical dosage form of claim 16, in the form of a drink.

22. The pharmaceutical composition of claim 1, wherein the fenofibrate has not been micronized.

23. The pharmaceutical composition of claim 1, wherein the fenofibrate has been micronized in the absence of a solid surfactant.

24. The pharmaceutical composition of claim 1, wherein the solubilizer comprises a combination of a vitamin E substance and at least one of a trialkyl citrate, and a lactone.

25. The pharmaceutical composition of claim 24, wherein the vitamin E substance is selected from the group consisting of tocopherols, tocopherol derivatives with organic acids, tocotrienols, individual enantiomers thereof, and mixtures of any of the foregoing.

26. The pharmaceutical composition of claim 25, wherein the vitamin E substance is selected from the group consisting of alpha-tocopherol, alpha-tocopheryl acetate, alpha-tocopheryl acid succinate, alpha-tocopheryl polyethylene glycol 1000 succinate, individual enantiomers thereof; and mixtures of any of the foregoing.

27. The method of claim 10, wherein the lipid disorder is an above-normal level of cholesterol.

28. The method of claim 10, wherein the lipid disorder is an above-normal triglyceride level.

29. The method of claim 10, wherein the lipid disorder is a below-normal level of high density lipoproteins.

30. The pharmaceutical composition of claim 26, wherein said vitamin E substance is alpha-tocopheryl polyethylene glycol 1000 succinate or an individual enantiomer thereof.

31. The pharmaceutical composition of claim 26, wherein said vitamin E substance comprises a mixture of alpha-tocopheryl polyethylene glycol 1000 succinate and alpha-tocopherol.

32. The pharmaceutical composition of claim 26, selected from the group consisting of d-alpha-tocopherol, d,1-alpha-tocopherol, d-alpha-tocopheryl acetate, and d,1-alpha-tocopheryl acetate.

33. The pharmaceutical composition or claim 26, wherein said vitamin E substance is alpha-tocopherol or an individual enantiomer thereof.

* * * * *